United States Patent
Jubran et al.

(10) Patent No.: US 7,316,877 B2
(45) Date of Patent: Jan. 8, 2008

(54) BISAZO-BASED CHARGE TRANSPORT MATERIALS HAVING 4-OXO-2,5-CYCLOHEXADIENE-1-YLIDENYL GROUPS

(75) Inventors: Nusrallah Jubran, St. Paul, MN (US); Patrick Knoll, St. Paul, MN (US)

(73) Assignee: Samsung Electronics Co., Ltd. (KR)

( * ) Notice: Subject to any disclaimer, the term of this patent is extended or adjusted under 35 U.S.C. 154(b) by 321 days.

(21) Appl. No.: 10/976,473

(22) Filed: Oct. 29, 2004

(65) Prior Publication Data

US 2006/0093932 A1   May 4, 2006

(51) Int. Cl.
*G03G 5/06* (2006.01)
*G03G 15/00* (2006.01)
*C07C 249/00* (2006.01)

(52) U.S. Cl. .................. 430/70; 430/72; 564/249; 399/159

(58) Field of Classification Search ............. 430/58.35, 430/58.4, 58.65, 70
See application file for complete search history.

(56) References Cited

U.S. PATENT DOCUMENTS 6,268,095 B1 * 7/2001 Kuroda .................. 430/58.35
6,287,736 B1 * 9/2001 Takaki et al. ............ 430/58.35
6,472,514 B2   10/2002 Kuroda
6,485,873 B1 * 11/2002 Ohkura et al. ............... 430/83

FOREIGN PATENT DOCUMENTS

JP       2003-270818  *  9/2003

OTHER PUBLICATIONS

Bethell, Donald, Kang, Dong-Hyo, and Zerbi, Giuseppe, *Oligormeric bis(1,3-indandiylidene)azines: preparation, electrochemical and spectroscopic properties, and implications for the use of polyazines as conducting material*, J. Chem. Soc., Perkin Trans. 2, 1996, pp. 1081-1086.

* cited by examiner

*Primary Examiner*—Mark F. Huff
*Assistant Examiner*—Peter Vajda
(74) *Attorney, Agent, or Firm*—Patterson, Thuente, Skaar & Christensen, P.A.

(57) ABSTRACT

Improved organophotoreceptor comprises an electrically conductive substrate and a photoconductive element on the electrically conductive substrate, the photoconductive element comprising:

(c) a charge transport material having the formula:

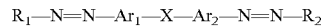

where $R_1$ and $R_2$ comprise, each independently, a 4-oxo-2,5-cyclohexadiene-1-ylidenyl group;
X comprises oxy, thio, sulfonyl, sulfinyl, sulfonyldioxy, azo, carbonyl, thiocarbonyl, carbonyldioxy, oxalyl, an arylene group, an arylenebisazo group, an imino group, a hydrazo group, a carbonimidoyl group, a vinylene group, or a combination thereof; and
$Ar_1$ and $Ar_2$ comprise, each independently, an aromatic group; and (b) a charge generating compound.

Corresponding electrophotographic apparatuses, imaging methods, and the charge transport material are also described.

26 Claims, No Drawings

BISAZO-BASED CHARGE TRANSPORT MATERIALS HAVING 4-OXO-2,5-CYCLOHEXADIENE-1-YLIDENYL GROUPS

FIELD OF THE INVENTION

This invention relates to organophotoreceptors suitable for use in electrophotography and, more specifically, to organophotoreceptors including a charge transport material having two azo groups each bonded to a 4-oxo-2,5-cyclohexadiene-1-ylidenyl group.

BACKGROUND OF THE INVENTION

In electrophotography, an organophotoreceptor in the form of a plate, disk, sheet, belt, drum, or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

Organophotoreceptors may be used for both dry and liquid electrophotography. There are many differences between dry and liquid electrophotography. In both dry and liquid electrophotography, the charge transport material used for the organophotoreceptor should be compatible with the polymeric binder in the photoconductive element. The selection of a suitable polymeric binder for a particular charge transport material can place constraints on the formation of the photoconductive element. If the charge transport material is not compatible with the polymeric binder, the charge transport material may phase-separate or crystallize in the polymeric binder matrix, or may diffuse onto the surface of the layer containing the charge transport material. If such incompatibility occurs, the organophotoreceptor can cease to transport charges.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising:

(a) a charge transport material having the formula:

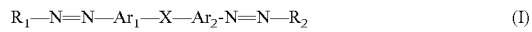

$$R_1-N=N-Ar_1-X-Ar_2-N=N-R_2 \qquad (I)$$

where $R_1$ and $R_2$ comprise, each independently, a 4-oxo-2,5-cyclohexadiene-1-ylidenyl group;

X comprises oxy, thio, sulfonyl, sulfinyl, sulfonyldioxy, azo, carbonyl, thiocarbonyl, carbonyldioxy, oxalyl, an arylene group such as a phenylene group, an arylenebisazo group such as a phenylenebisazo group, an imino group such as $NR_3$, a hydrazo group such as $R_4N-NR_5$, a carbonimidoyl group such as $C=NR_6$, a vinylene group such as $R_7C=CR_8$, or a combination thereof where $R_3$, $R_4$, $R_5$, $R_6$, $R_7$, and $R_9$ comprise, each independently, H, an alkyl group, an alkenyl group, such as a vinyl group, an allyl group, and a 2-phenylethenyl group, an alkynyl group, an acyl group, a heterocyclic group, an aromatic group, or a combination thereof; and $Ar_1$ and $Ar_2$ comprise, each independently, an aromatic group; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a toner dispenser, such as a liquid toner dispenser. The method of electrophotographic imaging with photoreceptors containing the above noted charge transport materials is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having Formula (I) above.

The invention provides suitable charge transport materials for organophotoreceptors featuring a combination of good mechanical and electrostatic properties. These photoreceptors can be used successfully with toners, such as liquid toners and dry toners, to produce high quality images. The high quality of the imaging system can be maintained after repeated cycling.

Other features and advantages of the invention will be apparent from the following description of the particular embodiments thereof, and from the claims.

DETAILED DESCRIPTION OF PREFERRED EMBODIMENTS

An organophotoreceptor as described herein has an electrically conductive substrate and a photoconductive element including a charge generating compound and a charge transport material having two azo groups each bonded to a 4-oxo-2,5-cyclohexadiene-1-ylidenyl group. The two azo groups are linked together through an X group where the X group may be oxy, thio, sulfonyl, sulfinyl, sulfonyldioxy, azo, carbonyl, thiocarbonyl, carbonyldioxy, oxalyl, an arylene group, an arylenebisazo group, an imino group, a hydrazo group, a carbonimidoyl group, a vinylene group, or a combination thereof. These charge transport materials have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

Charge transport materials may comprise monomeric molecules (e.g., N-ethyl-carbazolo-3-aldehyde N-methyl-N-phenyl-hydrazone), dimeric molecules (e.g., disclosed in U.S. Pat. Nos. 6,140,004, 6,670,085 and 6,749,978), or polymeric compositions (e.g., poly(vinylcarbazole)). The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamines such as triaryl amines, polyvinyl carbazole, polyvinyl pyrene, polyacenaphthylene, and the charge transport compounds described in U.S. Pat. Nos. 6,689,523, 6,670,085, 6,696,209, 6,749,978, and 6,768,010, and U.S. patent application Ser. Nos. 10/431,135, 10/431, 138, 10/699,364, 10/663,278, 10/699,581, 10/748,496, 10/789,094, 10/644,547, 10/749,174, 10/749,171, 10/749, 418, 10/699,039, 10/695,581, 10/692,389, 10/634,164, 10/749,164, 10/772,068, 10/749,178, 10/758,869, 10/695, 044, 10/772,069, 10/789,184, 10/789,077, 10/775,429, 10/670,483, 10/671,255, 10/663,971, 10/760,039, 10/815, 243, 10/832,596, 10/836,667, 10/814,938, 10/834,656, 10/815,118, 10/857,267, 10/865,662, 10/864,980, 10/865, 427, 10/883,453, 10/929,914, and 10/900,785. All the above patents and patent applications are incorporated herein by reference.

Non-limiting examples of electron transport compounds include, for example, bromoaniline, tetracyanoethylene, tetracyanoquinodimethane, 2,4,7-trinitro-9-fluorenone, 2,4,5, 7-tetranitro-9-fluorenone, 2,4,5,7-tetranitroxanthone, 2,4,8-trinitrothioxanthone, 2,6,8-trinitro-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene) malonate, anthraquinodimethane derivatives such as 11,11, 12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl) methylene]anthrone, 1,8-dihydroxy-10-[bis(ethoxycarbonyl)methylene]anthrone, and 1-cyano-10-[bis (ethoxycarbonyl)methylene)anthrone, 7-nitro-2-aza-9-fluorenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenyhnethane derivatives, tetracyano quinodimethane, 2,4,5,7-tetranitro-9-fluorenone, 2,4,7-trinitro-9-dicyanomethylene fluorenone, 2,4,5,7-tetranitroxanthone derivatives, 2,4,8-trinitrothioxanthone derivatives, 1,4,5,8-naphthalene bis-dicarboximide derivatives as described in U.S. Pat. Nos. 5,232,800, 4,468,444, and 4,442,193 and phenylazoquinolide derivatives as described in U.S. Pat. No. 6,472,514. In some embodiments of interest, the electron transport compound comprises an (alkoxycarbonyl-9-fluorenylidene)malononitrile derivative, such as (4-n-butoxycarbonyl-9-fluorenylidene)malononitrile, and 1,4,5,8-naphthalene bis-dicarboximide derivatives.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

(b) As described herein, an organophotoreceptor comprises a charge transport material having the formula:

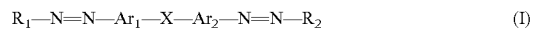

$$R_1-N=N-Ar_1-X-Ar_2-N=N-R_2 \qquad (I)$$

where $R_1$ and $R_2$ comprise, each independently, a 4-oxo-2,5-cyclohexadiene-1-ylidenyl group;

X comprises oxy, thio, sulfonyl, sulfinyl, sulfonyldioxy, azo, carbonyl, thiocarbonyl, carbonyldioxy, oxalyl, an arylene group such as a phenylene group, an arylenebisazo group such as a phenylenebisazo group, an imino group such as $NR_3$, a hydrazo group such as $R_4N-NR_5$, a carbonimidoyl group such as $C=NR_6$, a vinylene group such as $R_7C=CR_8$, or a combination thereof where $R_3$, $R_4$, $R_5$, $R_6$, $R_7$, and $R_8$ comprise, each independently, H, an alkyl group, an alkenyl group, such as a vinyl group, an allyl group, and a 2-phenylethenyl group, an alkynyl group, an acyl group, a heterocyclic group, an aromatic group, or a combination thereof; and $Ar_1$ and $Ar_2$ comprise, each independently, an aromatic group.

A heterocyclic group includes any monocyclic or polycyclic (e.g., bicyclic, tricyclic, etc.) ring compound having at least a heteroatom (e.g., O, S, N, P, B, Si, etc.) in the ring.

An aromatic group can be any conjugated ring system containing 4n+2 pi-electrons. There are many criteria available for determining aromaticity. A widely employed criterion for the quantitative assessment of aromaticity is the resonance energy. Specifically, an aromatic group has a resonance energy. In some embodiments, the resonance energy of the aromatic group is at least 10 KJ/mol. In further embodiments, the resonance energy of the aromatic group is greater than 0.1 KJ/mol. Aromatic groups may be classified as an aromatic heterocyclic group which contains at least a heteroatom in the 4n+2 pi-electron ring, or as an aryl group which does not contain a heteroatom in the 4n+2 pi-electron ring. The aromatic group may comprise a combination of aromatic heterocyclic group and aryl group. Nonetheless, either the aromatic heterocyclic or the aryl group may have at least one heteroatom in a substituent attached to the 4n+2 pi-electron ring. Furthermore, either the aromatic heterocyclic or the aryl group may comprise a monocyclic or polycyclic (such as bicyclic, tricyclic, etc.) ring.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4) dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6 di(10H-10-phenothiazinyl)hexane). The linking group may include an aliphatic group, an aromatic group, a heterocyclic group, or a combination thereof. Furthermore, the linking group may comprise at least one heteroatom such as O, S, Si, and N.

Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or by a linking group (as in stilbenyl, diphenyl sulfone, an arylamine group). The linking group may include an aliphatic group, an aromatic group, a heterocyclic group, or a combination thereof. Furthermore, the linking group may comprise at least one heteroatom such as O, S, Si, and N.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, alkenyl group, alkynyl group, aromatic group such as phenyl group and triarylamino group, heterocyclic group such as carbazoylyl group, arylene group such as phenylene group, arylenebisazo group, imino group, hydrazo group, carbonimidoyl group, vinylene group, 4-oxo-2,5-cyclohexadiene-1-ylidenyl group, etc.) may have any substituent thereon which is consistent with the bond structure of that group. For example, where the term 'alkyl group' or 'alkenyl group' is used, that term would not only include unsubstituted linear, branched and cyclic alkyl group or alkenyl group, such as methyl, ethyl, ethenyl or vinyl, isopropyl, tert-butyl, cyclohexyl, cyclohexenyl, dodecyl and the like, but also substituents having heteroatom(s), such as 3-ethoxylpropyl, 4-(N, N-diethylamino)butyl, 3-hydroxypentyl, 2-thiolhexyl, 1,2,3-tribromoopropyl, and the like, and aromatic group, such as phenyl, naphthyl, carbazolyl, pyrrole, and the like. However, as is consistent with such nomenclature, no substitution would be included within the term that would alter the fundamental bond structure of the underlying group. For example, where a phenyl group is recited, substitution such as 2- or 4-aminophenyl, 2- or 4-(N,N-disubstituted)aminophenyl, 2,4-dihydroxyphenyl, 2,4,6-trithiophenyl, 2,4,6-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester [e.g., poly(ethylene terephthalate) or poly(ethylene naphthalate)], polyimide, polysulfone, polypropylene, nylon, polyester, polycarbonate, polyvinyl resin, poly(vinyl fluoride), polystyrene and the like. Specific examples of polymers for supporting substrates included, for example, polyethersulfone (STABAR™ S-100, available from ICI), poly(vinyl fluoride) (TEDLAR®, available from E.I. DuPont de Nemours & Company), polybisphenol-A polycarbonate (MAKROFOL™, available from Mobay Chemical Company) and amorphous poly(ethylene terephthalate) (MELINAR™, available from ICI Americas, Inc.). The electrically conductive materials may be graphite, dispersed carbon black, iodine, conductive polymers such as polypyrroles and CALGON® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers (such as a dye or pigment). Non-limiting examples of suitable charge generating compounds include, for example, metal-free phthalocyanines (e.g., ELA 8034 metal-free phthalocyanine available from H. W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name INDOFAST™ Double Scarlet, INDOFAST™ Violet Lake B, INDOFAST™ Brilliant Scarlet and INDOFAST™ Orange, quinacridones available from DuPont under the trade name MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazopigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. LV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425, 333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

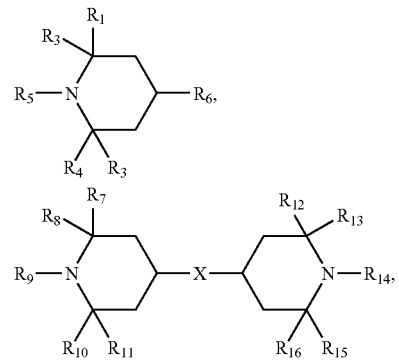

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, each independently, hydrogen, alkyl group, or ester, or ether group; and $R_5$, $R_9$, and $R_{14}$ are, each independently, alkyl group; and X is a linking group selected from the group consisting of —O—CO—$(CH_2)_m$—CO—O— where m is between 2 to 20.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, poly(styrene-co-butadiene), poly(styrene-co-acrylonitrile), modified acrylic polymers, poly(vinyl acetate), styrene-alkyd resins, soya-alkyl resins, poly(vinylchloride), poly(vinylidene chloride), polyacrylonitrile, polycarbonates, poly(acrylic acid), polyacrylates, polymethacrylates, styrene polymers, poly(vinyl butyral), alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether-co-dicyclopentadiene), copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. Iupilon-A from Mitsubishi Engineering Plastics, or Lexan 145 from General Electric); polycarbonate Z which is derived from cyclohexylidene bisphenol (e.g. Iupilon-Z from Mitsubishi Engineering Plastics Corp, White Plain, N.Y.); and polycarbonate C which is derived from methylbisphenol A (from Mitsubishi Chemical Corporation). Non-limiting examples of suitable polyester binders include ortho-polyethylene terephthalate (e.g. OPET TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport material generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport material and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as poly(vinyl alcohol), methyl vinyl ether/maleic anhydride copolymer, casein, poly(vinyl pyrrolidone), poly(acrylic acid), gelatin, starch, polyurethanes, polyimides, polyesters, polyamides, poly(vinyl acetate), poly(vinyl chloride), poly(vinylidene chloride), polycarbonates, poly(vinyl butyral), poly(vinyl acetoacetal), poly(vinyl formal), polyacrylonitrile, poly(methyl methacrylate), polyacrylates, poly(vinyl carbazoles), copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as filmed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked olymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, poly(methyl methacrylate), poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, cellulosics and the like. In some embodiments, the sub-layer has a dry thickness between about 20 Angstroms and about 20,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," and 2002/0086916, entitled "Liquid Inks Comprising Treated Colorant Particles," and U.S. Pat. No. 6,649,316, entitled "Phase Change Developer For Liquid Electrophotography," all three of which are incorporated herein by reference.

Charge Transport Material

As described herein, an organophotoreceptor comprises a charge transport material having the formula:

$$R_1-N=N-Ar_1-X-Ar_2-N=N-R_2 \tag{I}$$

where $R_1$ and $R_2$ comprise, each independently, a 4-oxo-2,5-cyclohexadiene-1-ylidenyl group;

X comprises oxy, thio, sulfonyl, sulfinyl, sulfonyldioxy, azo, carbonyl, thiocarbonyl, carbonyldioxy, oxalyl, an arylene group such as a phenylene group, an arylenebisazo group such as a phenylenebisazo group, an imino group such as $NR_3$, a hydrazo group such as $R_4N-NR_5$, a carbonimidoyl group such as $C=NR_6$, a vinylene group such as $R_7C=CR_8$, or a combination thereof where $R_3$, $R_4$, $R_5$, $R_6$, $R_7$, and $R_8$ comprise, each independently, H, an alkyl group, an alkenyl group, such as a vinyl group, an allyl group, and a 2-phenylethenyl group, an alkynyl group, an acyl group, a heterocyclic group, an aromatic group, or a combination thereof; and $Ar_1$ and $Ar_2$ comprise, each independently, an aromatic group.

In some embodiments of interest, the $Ar_1$ and $Ar_2$ groups of Formula (I) comprise, each independently, a phenylene group, a triarylamino group, or a carbazolyl group. In other embodiments, the $R_1$ and $R_2$ groups of Formula (I) have, each independently, the following formula:

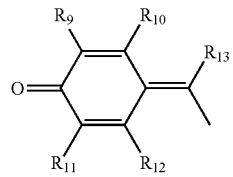

where $R_9$, $R_{10}$, $R_{11}$, $R_{12}$, and $R_{13}$ comprise, each independently, H, a halogen, nitro, nitroso, cyano, hydroxyl, thiol, carboxyl, an amino group, an alkyl group, an alkenyl group, an alkynyl group, an acyl group, an amido group, a heterocyclic group, an aromatic group, a part of a ring group, such as cycloalkyl groups, heterocyclic groups, and a benzo group, or a combination thereof. In further embodiments, the $Ar_1$ and $Ar_2$ groups comprise, each independently, a phenyl group. In additional embodiments, the $R_1$, $R_2$, $Ar_1$ and $Ar_2$ groups, each independently, further comprise at least a substituent selected from the group consisting of a halogen, a nitro, a nitroso, a cyano, an azo, a carboxyl, an ester group, a sulfonate group, a phosphate group, a phosphonate group, an alkyl group, an alkenyl group, an alkynyl group, an acyl group, an amido group, a heterocyclic group, an aromatic group, or a combination thereof.

Specific, non-limiting examples of suitable charge transport materials within Formula (I) of the present invention have the following structures, which may further comprise at least a substituent selected from the group consisting of a halogen, nitro, nitroso, cyano, azo, carboxyl, an ester group, a sulfonate group, a phosphate group, a phosphonate group, an alkyl group, an alkenyl group, an alkynyl group, an acyl group, an amido group, a heterocyclic group, an aromatic group, or a combination thereof.

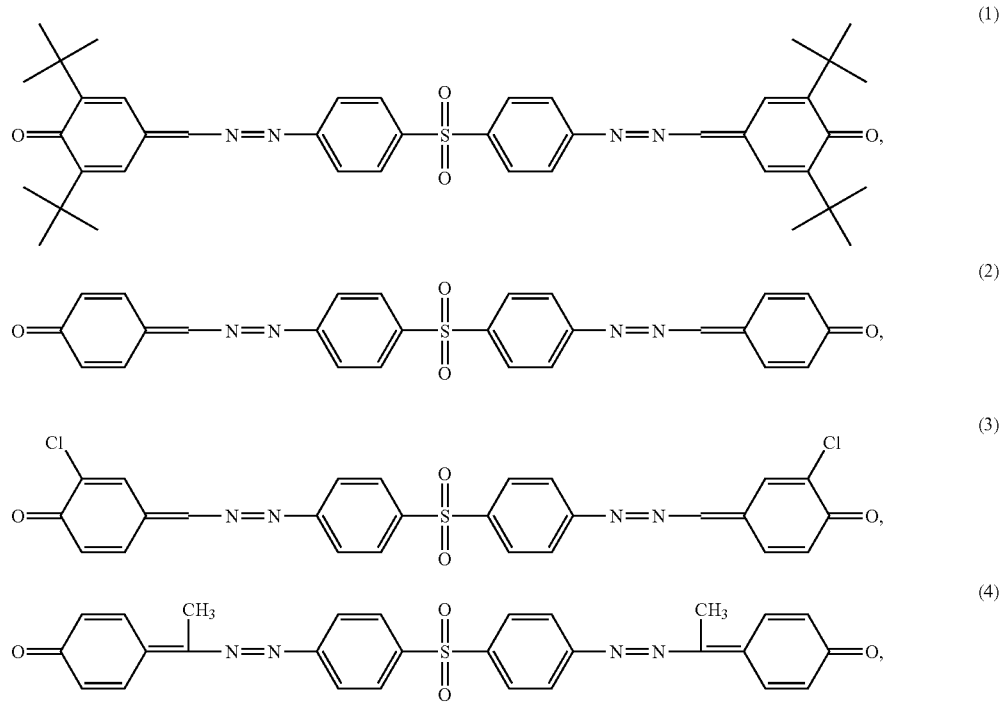

-continued
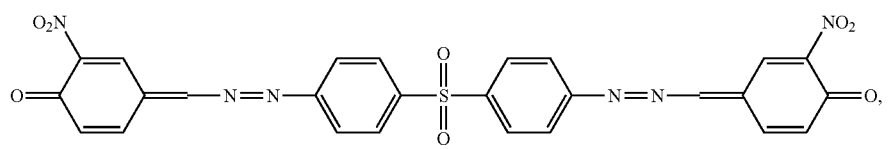
(5)
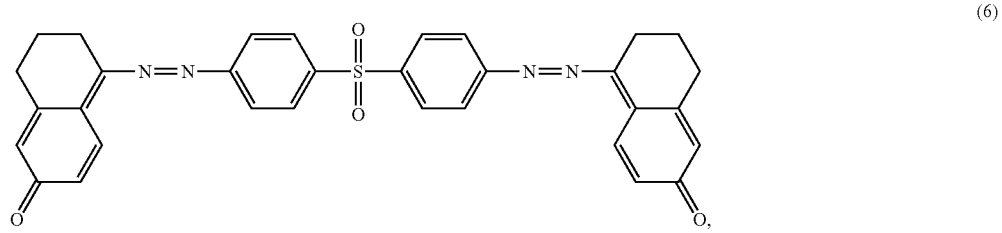
(6)
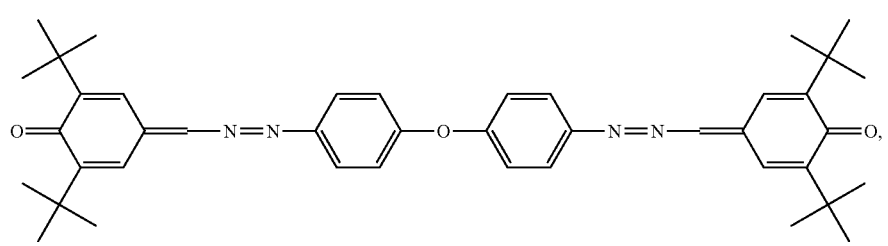
(7)
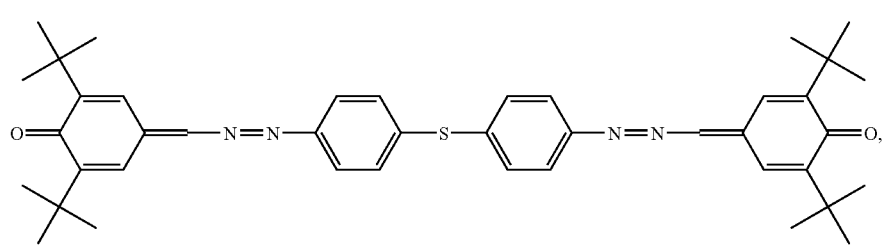
(8)
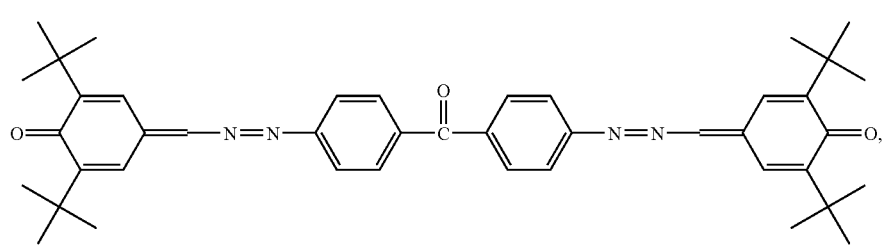
(9)
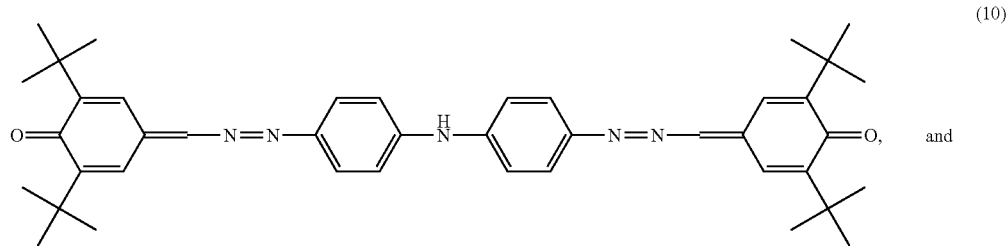
(10) and
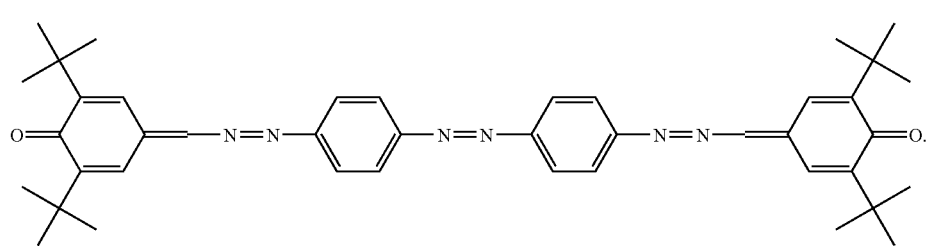
(11)

Synthesis of Charge Transport Materials

The synthesis of the charge transport materials of this invention can be prepared by the following multi-step synthetic procedure, although other suitable procedures can be used by a person of ordinary skill in the art based on the disclosure herein.

General Synthetic Procedure for Charge Transport Materials of Formula (I)

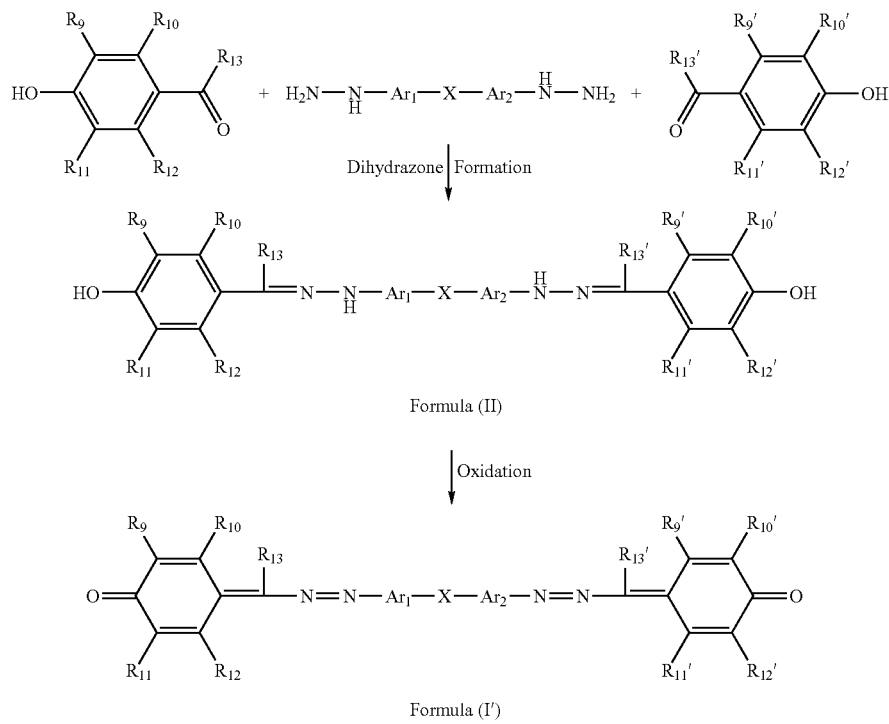

Preparation of Dihydrazine Compounds. The dihydrazine compounds having the general formula $H_2N-NH-Ar_1-X-Ar_2-NH-NH_2$ may be prepared by any of the synthetic methods known in the art for their preparartions. X may comprise oxy, thio, sulfonyl, sulfinyl, sulfonyldioxy, azo, carbonyl, thiocarbonyl, carbonyldioxy, oxalyl, an arylene group, an arylenebisazo group, an imino group, a hydrazo group, a carbonimidoyl group, a vinylene group, or a combination thereof. $Ar_1$ and $Ar_2$ may comprise, each independently, an aromatic group.

In some embodiments of interest, the dihydrazine compound is $H_2N-NH-C_6H_4-SO_2-C_6H_4-NH-NH_2$, where $Ar_1$ and $Ar_2$ are phenylene and X is sulfonyl. The dihydrazine compound $H_2N-NH-C_6H_4-SO_2-C_6H_4-NH-NH_2$ may be prepared according to the procedure described in Japanese Patent No. 32006632 where a mixture of 700 g of hydrazine ($N_2H_4.H_2O$, 80%) and 100 g of bis(4-chlorophenyl) sulfone is refluxed for 20 hours. After the reaction mixture is cooled, the precipitate is filtered off. Next, the precipitate is dissolved in 500 ml of 5% hydrochloric acid, and the solution is filtered with carbon. After the filtrate is acidified with a mixture of sodium acetate and acetic acid, the precipitate is filtered off to yield the product. Alternatively, the dihydrazine compound $H_2N-NH-C_6H_4-SO_2-C_6H_4-NH-NH_2$ may also be prepared according to the procedures described in Japanese Patent No. 26006916 and the article by Heymann et al., *J. Am. Chem. Soc.*, Vol. 67, pp 1986-90 (1945) where 4,4'-diaminodiphenyl sulfone [$(p-H_2C_6H_4)_2SO_2$] in diluted hydrochloric acid is diazotized with a diazotizing agent such as sodium nitrite. The diazotized compound is then reduced by a reducing agent such as tin(II) chloride and sodium sulfite to yield the product. All of the above-mentioned Japanese patents and article are incorporated herein by reference.

In other embodiments of interest, the dihydrazine compound is $H_2N-NH-C_6H_4-O-C_6H_4-NH-NH_2$, where $Ar_1$ and $Ar_2$ are phenylene and X is O. The dihydrazine compound $H_2N-NH-C_6H_4-O-C_6H_4-NH-NH_2$ may be prepared similarly by the procedure described in Japanese Patent No. 26006916 and the article by Heymann et al., *J. Am. Chem. Soc.*, Vol. 67, pp 1986-90 (1945) except that 4,4'-diaminodiphenyl sulfone is replaced with 4,4'-oxydianiline (available from Aldrich, Milwaukee, Wis.).

In other embodiments of interest, the dihydrazine compound is $H_2N-NH-C_6H_4-S-C_6H_4-NH-NH_2$, where $Ar_1$ and $Ar_2$ are phenylene and X is S. The dihydrazine compound $H_2N-NH-C_6H_4-S-C_6H_4-NH-NH_2$ may be prepared similarly by the procedure described in Japanese Patent No. 26006916 and the article by Heymann et al., *J. Am. Chem. Soc.*, Vol. 67, pp 1986-90 (1945) except that 4,4'-diaminodiphenyl sulfone is replaced with 4,4'-diaminodiphenyl sulfide (available from Aldrich, Milwaukee, Wis.).

In other embodiments of interest, the dihydrazine compound is $H_2N-NH-C_6H_4-C(=O)-C_6H_4-NH-NH_2$, where $Ar_1$ and $Ar_2$ are phenylene and X is carbonyl. The dihydrazine compound $H_2N-NH-C_6H_4-C(=O)-C_6H_4-NH-NH_2$ may be prepared similarly by the procedure described in Japanese Patent No. 26006916 and the article by Heymann et al., *J. Am. Chem. Soc.*, Vol. 67, pp 1986-90 (1945) except that 4,4'-diaminodiphenyl sulfone is replaced with 4,4'-diaminobenzophenone (available from Aldrich, Milwaukee, Wis.). Alternatively, the dihydrazine compound $H_2N-NH-C_6H_4-C(=O)-C_6H_4-NH-NH_2$ may also be prepared according to the procedures described in Japanese Patent No. 32006632 except that bis(4-chlorophenyl) sulfone is replaced with 4,4'-dichlorobenzophenone (available from Aldrich, Milwaukee, Wis.).

In further embodiments of interest, the dihydrazine compound is $H_2N-NH-C_6H_4-NH-C_6H_4-NH-NH_2$, where $Ar_1$ and $Ar_2$ are phenylene and X is NH. The dihydrazine compound $H_2N-NH-C_6H_4-NH-C_6H_4-NH-NH_2$ may be prepared similarly by the procedure described in Japanese Patent No. 26006916 and the article by Heymann et al., *J. Am. Chem. Soc.*, Vol. 67, pp 1986-90 (1945) except that 4,4'-diaminodiphenyl sulfone is replaced with 4,4'-diaminodiphenylamine sulfate salt (available from Aldrich, Milwaukee, Wis.).

In additional embodiments of interest, the dihydrazine compound is $H_2N-NH-C_6H_4-N=N-C_6H_4-NH-NH_2$, where $Ar_1$ and $Ar_2$ are phenylene and X is azo. The dihydrazine compound $H_2N-NH-C_6H_4-N=N-C_6H_4-NH-NH_2$ may be prepared similarly by the procedure described in Japanese Patent No. 32006632 except that bis(4-chlorophenyl) sulfone is replaced with 1,2-bis(4-chlorophenyl)diazene (available from Aldrich, Milwaukee, Wis.).

Other suitable dihydrazine compounds, where X may be sulfinyl, sulfonyldioxy, thiocarbonyl, carbonyldioxy, oxalyl, an arylene group, an arylenebisazo group, a hydrazo group, a carbonimidoyl group, or a vinylene group, may be prepared similarly based on the disclosure herein by a person of ordinary skill in the art.

Dihydrazone Compounds of Formula (II). The dihydrazone compounds of Formula (II) may be prepared by the reaction between the corresponding dihydrazine compounds having the general formula $H_2N-NH-Ar_1-X-Ar_2-NH-NH_2$ with two aromatic compounds having an acyl group and a hydroxyl group. Non-limiting examples of the aromatic compound having an acyl group and a hydroxyl group include Formulae (IIIA) and (IIIB) where $R_9$, $R_{10}$, $R_{11}$, $R_{12}$, $R_{13}$, $R_9'$, $R_{10}'$, $R_{11}'$, $R_{12}'$, and $R_{13}'$ comprise, each independently, H, a halogen, nitro, nitroso, cyano, hydroxyl, thiol, carboxyl, an amino group, an alkyl group, an alkenyl group, an alkynyl group, an acyl group, an amido group, a heterocyclic group, an aromatic group, a part of a ring group, or a combination thereof. The aromatic compounds of Formulae (IIIA) and (IIIB) may be the same (i.e., $R_9=R_9'$, $R_{10}=R_{10}'$, $R_{11}=R_{11}'$, $R_{12}=R_{12}'$, and $R_{13}=R_{13}'$) or different (i.e., $R_9 \neq R_9'$, $R_{10} \neq R_{10}'$, $R_{11} \neq R_{11}'$, $R_{12} \neq R_{12}'$, or $R_{13} \neq R_{13}'$). Non-limiting commercial available examples of aromatic compounds having an acyl group and a hydroxyl group include 3,5-di-tert-butyl-4-hydroxybenzaldehyde, 4-hydroxybenzaldehyde, 4-hydroxy-3-methylbenzaldehyde, 4'-hydroxyacetophenone, 3,4-dihydroxybenzaldehyde, 2,4-dihydroxybenzaldehyde, 5-hydroxy-1-indanone, 4-hydroxyisophthalaldehyde, 1-(4-hydroxy-3-methylphenyl) ethanone, 1-(4-hydroxy-2-methylphenyl)ethanone, 4'-hydroxypropiophenone, 4-hydroxy-3-nitrobenzaldehyde, 4-hydroxy-3,5-dimethylbenzaldehyde, 2',4'-dihydroxyacetophenone, 2,4-dihydroxy-6-methylbenzaldehyde, 1-(3,4-dihydroxyphenyl)ethanone, 2,4-dihydroxy-3-methylbenzaldehyde, 4-hydroxy-2-methoxybenzaldehyde, 2,3,4-trihydroxybenzaldehyde, 2,4,6-trihydroxybenzaldehyde, 2,4,5-trihydroxybenzaldehyde, 3,4,5-trihydroxybenzaldehyde, 3-chloro-4-hydroxybenzaldehyde, 6-hydroxy-1-tetralone, 1-(4-hydroxyphenyl)-1-butanone, 1-(4-hydroxy-3,5-dimethylphenyl)ethanone, 1-(4-hydroxy-2,5-dimethylphenyl)ethanone, 1-(4-hydroxy-2,6-dimethylphenyl)ethanone, 5-formylsalicylic acid, 1-(3-hydroxy-4-methoxyphenyl)ethanone, 1-(2,4-dihydroxy-6-methylphenyl)ethanone, 1-(2,4-dihydroxy-3-methylphenyl) ethanone, 1-(4-hydroxy-3-methoxyphenyl)ethanone, 3-ethoxy-4-hydroxybenzaldehyde, 1-(2,4-dihydroxyphenyl)-1-propanone, 1-(2,4,6-trihydroxyphenyl)ethanone, 3,4-dihydroxy-5-methoxybenzaldehyde, and 1-(2,3,4-trihydroxyphenyl)ethanone. All of the above aromatic compounds having an acyl group and a hydroxyl group are available from commercial suppliers such as Aldrich. In some embodiments, the aromatic compounds of Formulae (IIIA) and (IIIB) are the same and they may react with the dihydrazine compound simultaneously. In other embodiments, the aromatic compounds of Formulae (IIIA) and (IIIB) are different and they may react with the dihydrazine compound sequentially or simulatneously. The dihydrazone formation reaction may be catalyzed by an acid such as sulfuric acid and hydrochloric acid.

Charge Transport Material of Formula (1). Some non-limiting examples of the the charge transport material of Formula (I) include compounds representing by Formula (I'). The charge transport material of Formula (I') may be prepared by oxidizing the dihydrazone of Formula (I) by an oxidizing agent such as potassium permanganate and manganese oxide. The desired product may be isolated and purified by the conventional purification techniques such as column chromatography and recrystallization. The oxidation of alcohols to the corresponding aldehdyes or ketones are described in Carey et al., "Advanced Organic Chemistry, Part B: Reactions and Synthesis," 2nd Edition, pp. 481-490 (1983), which is incorporated herein by reference.

The invention will now be described further by way of the following examples.

EXAMPLES

Example 1

Synthesis And Characterization Charge Transport Materials

This example describes the synthesis and characterization of Compounds (1)-(11) in which the numbers refer to formula numbers above. The characterization involves chemical characterization of the compositions. The electrostatic characterization, such as mobility, of the materials formed with the compositions is presented in a subsequent example.

Compound (1)

A mixture of 3,5-di-tert-butyl-4-hydroxybenzaldehyde (8.76 g, 0.036 mol, available from Aldrich), 1,1'-(sulfonyl-di-1,4-phenylene)bishydrazine (5.00 g, 0.018 mol, available from Vitas-M, Moscow, Russia; Phone: 70959395737) and tetrahydrofuran (1.1 L, THF) was added to a 2 L three-neck round-bottom flask equipped with a stirring bar and a reflux condenser. The reaction mixture was stirred and refluxed until all the starting materials went into solution. After ten drops of 37% hydrochloric acid was added, the reaction mixture was allowed to reflux for four additional hours. After refluxing, the solution was evaporated down to about 50 mL using a rotary evaporator. After the evaporation, the dihydrazone product precipitated and was collected by filtration. Next, ethanol (about 100 ml) was slowly added to the remaining solution until precipitate formed and the solution was chilled in a refrigerator overnight. After chilling, the solution failed to yield any more dihydrazone product. The solvent was evaporated away to yield a sticky solid. The sticky solid was dissolved in THF (about 50 ml) until the residue was completely dissolved, and ethanol (about 100 ml) was slowly added to the solution until precipitate formed. Next, the filtrate was placed in the refrigerator for three hours to yield more precipitate of the dihydrazone product. The precipitate was collected by filtration and the filtrate was evaporated to yield more solid, which was collected and dried. The total sum of the dihydrazone product was 7.6 g (90%).

A mixture of the dihydrazone from the previous step (4.67 g, 0.010 mol) and manganese oxide (8.7 g, 0.100 mol, obtained form Aldrich) dissolved in 300 mL of chloroform was added to a 500 mL round-bottom flask equipped with a mechanical stirrer. After the reaction mixture was then stirred at room temperature for three hours, it was filtered. The filtrate was passed through a silica gel bed (grade 62 silica gel, 60-200 mesh, 150 Å, available from Aldrich) twice, and then evaporated in a rotary evaporator to yield a purple product. The purple product was then collected and dried in a 40° C. vacuum oven overnight. The yield of the purple product, Compound (1), was 2.90 g (70%).

Compound (2)

Compound (2) may be prepared by the procedure for Compound (1) except that 3,5-di-tert-butyl-4-hydroxybenzaldeyhe is replaced with 4-hydroxybenzaldehyde (available from Aldrich).

Compound (3)

Compound (3) may be prepared by the procedure for Compound (1) except that 3,5-di-tert-butyl-4-hydroxybenzaldeyhe is replaced with 3-chloro-4-hydroxybenzaldehyde (available from Aldrich).

Compound (4)

Compound (4) may be prepared by the procedure for Compound (1) except that 3,5-di-tert-butyl-4-hydroxybenzaldeyhe is replaced with 4'-hydroxyacetophenone (available from Aldrich).

Compound (5)

Compound (5) may be prepared by the procedure for Compound (1) except that 3,5-di-tert-butyl-4-hydroxybenzaldeyhe is replaced with 4-hydroxy-3-nitrobenzaldehyde (available from Aldrich).

Compound (6)

Compound (6) may be prepared by the procedure for Compound (1) except that 3,5-di-tert-butyl-4-hydroxybenzaldeyhe is replaced with 6-hydroxy-1-tetralone (available from Aldrich).

Compound (7)

Compound (7) may be prepared by the procedure for Compound (1) except that 1,1'-(sulfonyl-di-1,4-phenylene) bishydrazine is replaced with 4,4'-dihydrazinodiphenyl ether. 4,4'-Dihydrazinodiphenyl ether may be prepared according to a procedure similar to those described in Japanese Patent No. 26006916 and the article by Heymann et al., J. Am. Chem. Soc., Vol. 67, pp 1986-90 (1945) where 4,4-oxydianiline (available from Aldrich, Milwaukee, Wis.) in diluted hydrochloric acid is diazotized with a diazotizing agent such as sodium nitrite. The diazotized compound is then reduced by a reducing agent, such as tin(II) chloride and sodium sulfite, to yield the product.

Compound (8)

Compound (8) may be prepared by the procedure for Compound (1) except that 1,1'-(sulfonyl-di-1,4-phenylene) bishydrazine is replaced with 4,4'-dihydrazinodiphenyl sulfide. 4,4'-Dihydrazinodiphenyl sulfide may be prepared according to a procedure similar to those described in Japanese Patent No. 26006916 and the article by Heymann et al., J. Am. Chem. Soc., Vol. 67, pp 1986-90 (1945) where 4,4'-diaminodiphenyl sulfide (available from Aldrich, Milwaukee, Wis.) in diluted hydrochloric acid is diazotized with a diazotizing agent such as sodium nitrite. The diazotized compound is then reduced by a reducing agent, such as tin(II) chloride and sodium sulfite, to yield the product.

Compound (9)

Compound (9) may be prepared by the procedure for Compound (1) except that 1,1'-(sulfonyl-di-1,4-phenylene) bishydrazine is replaced with 4,4'-dihydrazinobenzophenone. 4,4'-Dihydrazinobenzophenone may be prepared according to a procedure similar to those described in Japanese Patent No. 26006916 and the article by Heymann et al., J. Am. Chem. Soc., Vol. 67, pp 1986-90 (1945) where 4,4'-diaminobenzophenone (available from Aldrich, Milwaukee, Wis.) in diluted hydrochloric acid is diazotized with a diazotizing agent such as sodium nitrite. The diazotized compound is then reduced by a reducing agent, such as tin(II) chloride and sodium sulfite, to yield the product.

Compound (10)

Compound (10) may be prepared by the procedure for Compound (1) except that 1,1'-(sulfonyl-di-1,4-phenylene) bishydrazine is replaced with 4,4'-dihydrazinodiphenylamine. 4,4'-Dihydrazinodiphenylamine may be prepared according to a procedure similar to those described in Japanese Patent No. 26006916 and the article by Heymann et al., J. Am. Chem. Soc., Vol. 67, pp 1986-90 (1945) where 4,4'-diaminodiphenylamine sulfate salt (available from Aldrich, Milwaukee, Wis.) is diazotized with a diazotizing agent such as sodium nitrite. Optionally, diluted hydrochloric acid may be added to the reaction mixture. The diazotized compound is then reduced by a reducing agent, such as tin(II) chloride and sodium sulfite, to yield the product.

Compound (11)

Compound (11) may be prepared by the procedure for Compound (1) except that 1,1'-(sulfonyl-di-1,4-phenylene) bishydrazine is replaced with 1,2-bis(4-dihydrazinophenyl) diazene. 1,2-Bis(4-dihydrazinophenyl)diazene may be prepared according to a procedure similar to that described in Japanese Patent No. 32006632 where a mixture of 700 g of hydrazine ($N_2H_4 \cdot H_2O$, 80%) and 100 g of 1,2-bis(4-chlorophenyl)diazene (available from Aldrich, Milwaukee, Wis.) is refluxed for 20 hours. After the reaction mixture is completed, the product is isolated and purified by conventional purification techniques such as recrystallization and chromatography.

Example 2

Charge Mobility Measurements

This example describes the measurement of charge mobility and ionization potential for charge transport materials, specifically Compound (1).

Sample 1

A mixture of 0.1 g of the Compound (1) and 0.1 g of polycarbonate Z was dissolved in 2 ml of tetrahydrofuran. The solution was coated on the polyester film with conductive Al layer by the dip roller method. After drying for 1 hour at 80° C., a clear 10 μm thick layer was formed. The electron mobility of the sample was measured and the results are presented in Table 1.

Mobility Measurements

Each sample was corona charged positively up to a surface potential U and illuminated with 2 ns long nitrogen laser light pulse. The hole mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747-752, incorporated herein by reference. The electron mobility measurement was repeated with appropriate changes to the charging regime to charge the sample to different U values, which corresponded to different electric field strength inside the layer E. This dependence on electric field strength was approximated by the formula

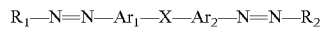

Here E is electric field strength, $\mu_0$ is the zero field mobility and $\alpha$ is Pool-Frenkel parameter. Table 1 lists the mobility characterizing parameters $\mu_0$ and $\alpha$ values and the mobility value at the $6.4 \times 10^5$ V/cm field strength as determined by these measurements for the samples.

TABLE 1

| Example | $\mu_0$ (cm$^2$/V · s) | $\mu$ (cm$^2$/V · s) at 6.4 · 10$^5$ V/cm | $\alpha$ (cm/V)$^{0.5}$ |
|---------|---------|---------|---------|
| Sample 1 | ~4.0 × 10$^{-11}$ | 2.4 × 10$^{-9}$ | ~0.0052 |

What is claimed is:

1. An organophotoreceptor comprising an electrically conductive substrate and a photoconductive element on the electrically conductive substrate, the photoconductive element comprising:
   (a) a charge transport material having the formula:

R$_1$—N=N—Ar$_1$—X—Ar$_2$—N=N—R$_2$ where R$_1$ and R$_2$ comprise, each independently, a 4-oxo-2,5-cyclohexadiene-1-ylidenyl group;
   X comprises oxy, thio, sulfonyl, sulfinyl, sulfonyldioxy, azo, carbonyl, thiocarbonyl, carbonyldioxy, oxalyl, an arylene group, an arylenebisazo group, an imino group, a hydrazo group, a carbonimidoyl group, a vinylene group, or a combination thereof; and
   Ar$_1$ and Ar$_2$ comprise, each independently, an aromatic group; and
   (b) a charge generating compound.

2. An organophotoreceptor according to claim 1 wherein Ar$_1$ and Ar$_2$ comprise, each independently, a phenylene group, a triarylamino group, or a carbazolyl group.

3. An organophotoreceptor according to claim 1 wherein X is selected from the group consisting of a phenylenebisazo group, NR$_3$, R$_4$N—NR$_5$, C=NR$_6$, and R$_7$C=CR$_8$ where R$_3$, R$_4$, R$_5$, R$_6$, R$_7$, and R$_8$ comprise, each independently, H, an alkyl group, an alkenyl group, an alkynyl group, an acyl group, a heterocyclic group, an aromatic group, or a combination thereof.

4. An organophotoreceptor according to claim 1 wherein R$_1$ and R$_2$ have each independently, the following formula:

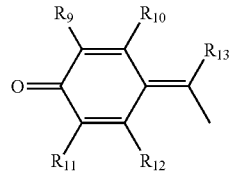

where R$_9$, R$_{10}$, R$_{11}$, R$_{12}$, and R$_{13}$ comprise, each independently, H, a halogen, nitro, nitroso, cyano, hydroxyl, thiol, carboxyl, an amino group, an alkyl group, an alkenyl group, an alkynyl group, an acyl group, an amido group, a heterocyclic group, an aromatic group, a part of a ring group, or a combination thereof.

5. An organophotoreceptor according to claim 4 wherein X comprises oxy, thio, or sulfonyl; and Ar$_1$ and Ar$_2$ comprise, each independently, a phenylene group.

6. An organophotoreceptor according to claim 1 wherein R$_1$, R$_2$, Ar$_1$ and Ar$_2$, each independently, further comprise at least a substituent selected from the group consisting of a halogen, nitro, nitroso, cyano, azo, carboxyl, an ester group, a sulfonate group, a phosphate group, a phosphonate group, an alkyl group, an alkenyl group, an alkynyl group, an acyl group, an amido group, a heterocyclic group, an aromatic group, or a combination thereof.

7. An organophotoreceptor according to claim 1 wherein the photoconductive element further comprises a second charge transport material.

8. An organophotoreceptor according to claim 7 wherein the second charge transport material comprises a charge transport compound.

9. An organophotoreceptor according to claim 1 wherein the photoconductive element further comprises a binder.

10. An electrophotographic imaging apparatus comprising:
    (a) a light imaging component; and
    (b) an organophotoreceptor oriented to receive light from the light imaging component, the organophotoreceptor comprising an electrically conductive substrate and a photoconductive element on the electrically conductive substrate, the photoconductive element comprising:
       (i) a charge transport material having the formula:

R$_1$—N=N—Ar$_1$—X—Ar$_2$—N=N—R$_2$ where R$_1$ and R$_2$ comprise, each independently, a 4-oxo-2,5-cyclohexadiene-1-ylidenyl group;
       X comprises oxy, thio, sulfonyl, sulfinyl, sulfonyldioxy, azo, carbonyl, thiocarbonyl, carbonyldioxy, oxalyl, an arylene group, an arylenebisazo group, an imino group, a hydrazo group, a carbonimidoyl group, a vinylene group, or a combination thereof; and
       Ar$_1$ and Ar$_2$ comprise, each independently, an aromatic group; and
       (ii) a charge generating compound.

11. An electrophotographic imaging apparatus according to claim 10 wherein Ar$_1$ and Ar$_2$ comprise, each independently, a phenylene group, a triarylamino group, or a carbazolyl group.

12. An electrophotographic imaging apparatus according to claim 10 wherein X is selected from the group consisting of a phenylenebisazo group, NR$_3$, R$_4$N—NR$_5$, C=NR$_6$, and R$_7$C=CR$_8$ where R$_3$, R$_4$, R$_5$, R$_6$, R$_7$, and R$_8$ comprise, each independently, H, an alkyl group, an alkenyl group, an alkynyl group, an acyl group, a heterocyclic group, an aromatic group, or a combination thereof.

13. An electrophotographic imaging apparatus according to claim 10 wherein $R_1$ and $R_2$ have each independently, the following formula:

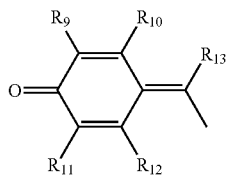

where $R_9$, $R_{10}$, $R_{11}$, $R_{12}$, and $R_{13}$ comprise, each independently, H, a halogen, nitro, nitroso, cyano, hydroxyl, thiol, carboxyl, an amino group, an alkyl group, an alkenyl group, an alkynyl group, an acyl group, an amido group, a heterocyclic group, an aromatic group, a part of a ring group, or a combination thereof.

14. An electrophotographic imaging apparatus according to claim 13 wherein X comprises oxy, thio, or sulfonyl; and $Ar_1$ and $Ar_2$ comprise, each independently, a phenyl group.

15. An electrophotographic imaging apparatus according to claim 10 wherein $R_1$, $R_2$, $Ar_1$ and $Ar_2$, each independently, further comprise at least a substituent selected from the group consisting of a halogen, nitro, nitroso, cyano, azo, carboxyl, an ester group, a sulfonate group, a phosphate group, a phosphonate group, an alkyl group, an alkenyl group, an alkynyl group, an acyl group, an amido group, a heterocyclic group, an aromatic group, or a combination thereof.

16. An electrophotographic imaging apparatus according to claim 10 wherein the photoconductive element further comprises a second charge transport material.

17. An electrophotographic imaging apparatus according to claim 16 wherein second charge transport material comprises a charge transport compound.

18. An electrophotographic imaging apparatus according to claim 10 further comprising a toner dispenser.

19. A charge transport material having the formula:

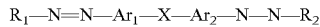

$R_1$—N=N—$Ar_1$—X—$Ar_2$—N—N—$R_2$ where $R_1$ and $R_2$ comprise, each independently, a 4-oxo-2,5-cyclohexadiene-1-ylidenyl group;

X comprises oxy, thio, sulfonyl, sulfinyl, sulfonyldioxy, azo, carbonyl, thiocarbonyl, carbonyldioxy, oxalyl, an arylene group, an arylenebisazo group, an imino group, a hydrazo group, a carbonimidoyl group, a vinylene group, or a combination thereof; and $Ar_1$ and $Ar_2$ comprise, each independently, an aromatic group.

20. A charge transport material according to claim 19 wherein $Ar_1$ and $Ar_2$ comprise, each independently, a phenylene group, a triarylamino group, or a carbazolyl group.

21. A charge transport material according to claim 19 wherein X is selected from the group consisting of a phenylenebisazo group, $NR_3$, $R_4N$—$NR_5$, C=$NR_6$, and $R_7C$=$CR_8$ where $R_3$, $R_4$, $R_5$, $R_6$, $R_7$, and $R_8$ comprise, each independently, H, an alkyl group, an alkenyl group, an alkynyl group, an acyl group, a heterocyclic group, an aromatic group, or a combination thereof.

22. A charge transport material according to claim 19 wherein $R_1$ and $R_2$ have each independently, the following formula:

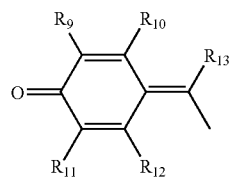

where $R_9$, $R_{10}$, $R_{11}$, $R_{12}$, and $R_{13}$ comprise, each independently, H, a halogen, nitro, nitroso, cyano, hydroxyl, thiol, carboxyl, an amino group, an alkyl group, an alkenyl group, an alkynyl group, an acyl group, an amido group, a heterocyclic group, an aromatic group, a part of a ring group, or a combination thereof.

23. A charge transport material according to claim 22 wherein X comprises oxy, thio, or sulfonyl; and $Ar_1$ and $Ar_2$ comprise, each independently, a phenyl group.

24. A charge transport material according to claim 19 wherein $R_1$, $R_2$, $Ar_1$ and $Ar_2$, each independently, further comprise at least a substituent selected from the group consisting of a halogen, nitro, nitroso, cyano, azo, carboxyl, an ester group, a sulfonate group, a phosphate group, a phosphonate group, an alkyl group, an alkenyl group, an alkynyl group, an acyl group, an amido group, a heterocyclic group, an aromatic group, or a combination thereof.

25. A charge transport material according to claim 19 selected from the group consisting of the following formulae:

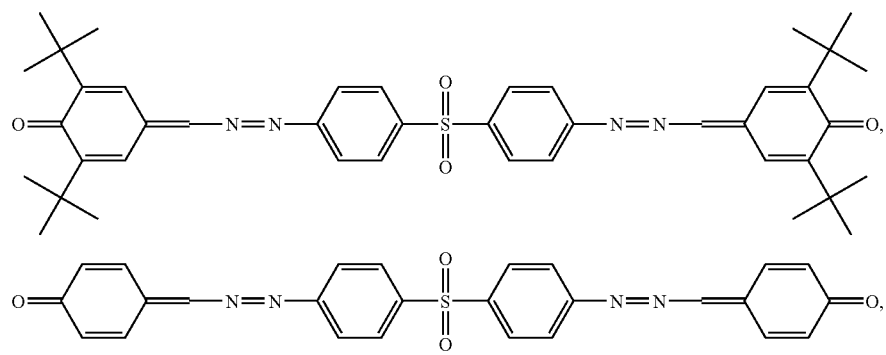

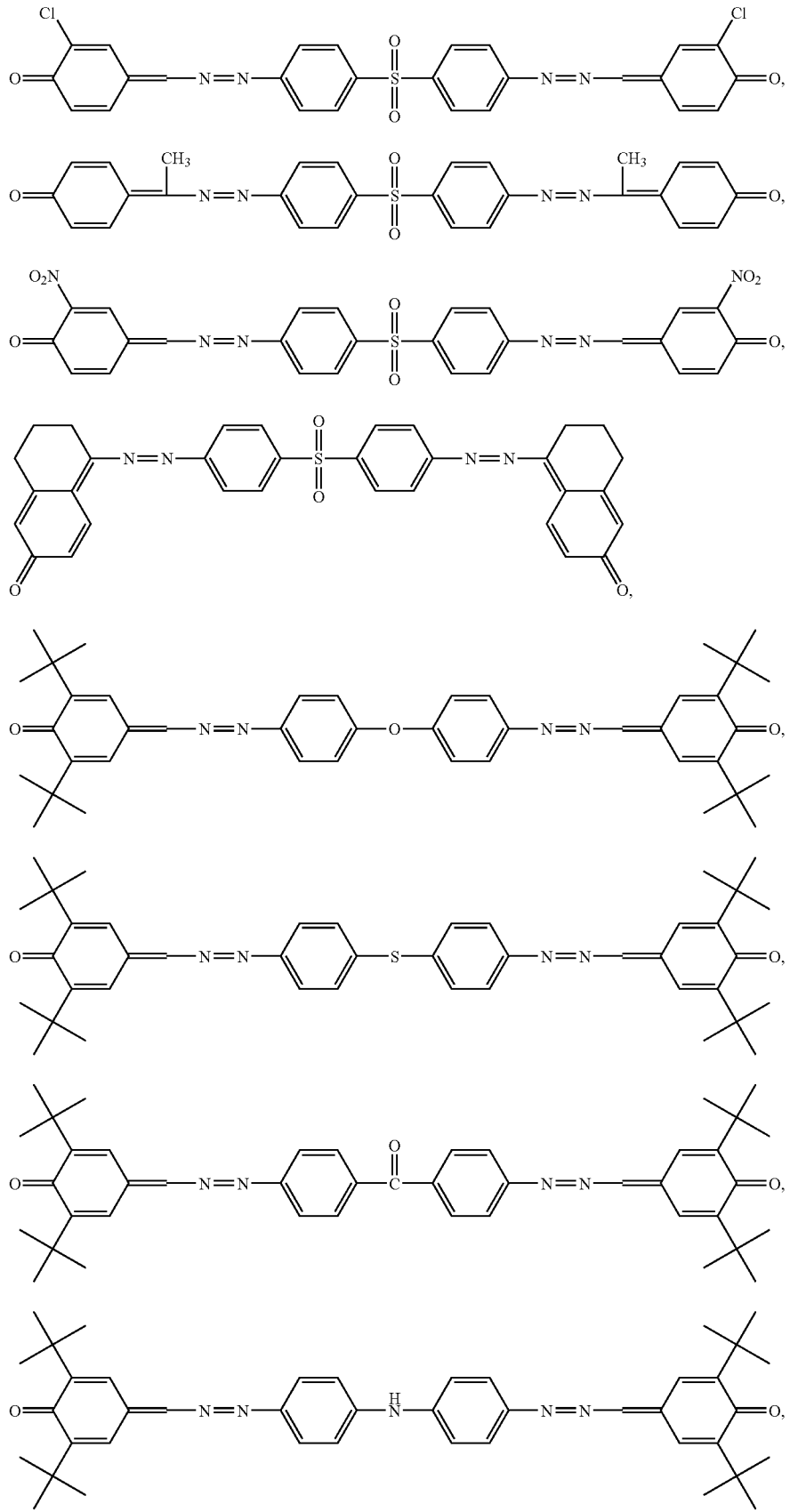

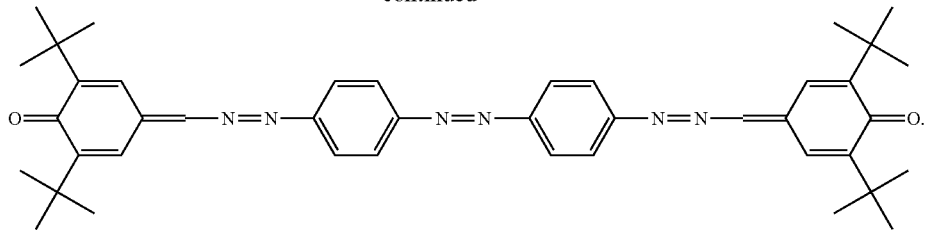

26. A charge transport material according to claim 25 further comprising at least a substituent selected from the group consisting of a halogen, nitro, nitroso, cyano, azo, carboxyl, an ester group, a sulfonate group, a phosphate group, a phosphonate group, an alkyl group, an alkenyl group, an alkynyl group, an acyl group, an amido group, a heterocyclic group, an aromatic group, or a combination thereof.

* * * * *